(12) United States Patent
Dieplinger et al.

(10) Patent No.: US 8,137,922 B2
(45) Date of Patent: Mar. 20, 2012

(54) METHOD FOR DIAGNOSING THE METABOLIC SYNDROME (MS)

(75) Inventors: Hans Dieplinger, Innsbruck (AT);
Florian Kronenberg, Innsbruck (AT);
Johann Willeit, Innsbruck (AT); Stefan Kiechl, Zirl (AT); Wolfgang Engel, Göttingen (DE)

(73) Assignee: Hans Dieplinger, Innsbruck (AT)

( * ) Notice: Subject to any disclaimer, the term of this patent is extended or adjusted under 35 U.S.C. 154(b) by 0 days.

(21) Appl. No.: 12/676,528

(22) PCT Filed: Sep. 4, 2008

(86) PCT No.: PCT/AT2008/000315
§ 371 (c)(1),
(2), (4) Date: Jun. 9, 2010

(87) PCT Pub. No.: WO2009/029971
PCT Pub. Date: Mar. 12, 2009

(65) Prior Publication Data
US 2010/0260771 A1      Oct. 14, 2010

(30) Foreign Application Priority Data
Sep. 4, 2007   (AT) ................................. A 1378/2007

(51) Int. Cl.
*G01N 33/53*   (2006.01)
(52) U.S. Cl. ........................ 435/7.1; 435/7.2; 436/518
(58) Field of Classification Search .................... None
See application file for complete search history.

(56) References Cited

U.S. PATENT DOCUMENTS
6,762,033 B2 *   7/2004   Illmensee et al. .............. 435/7.9

FOREIGN PATENT DOCUMENTS

| AT | 501 348 | 10/2008 |
|---|---|---|
| WO | WO 95/27059 | 10/1995 |
| WO | WO 01/01148 | 1/2001 |
| WO | WO 06/063332 | 6/2006 |
| WO | WO 06/079136 | 8/2006 |

OTHER PUBLICATIONS

Alexander et al. Diabetes 2003 vol. 52, p. 1210-1214.*
Grundy, "Drug therapy of the metabolic syndrome: minimizing the emerging crisis in polypharmacy," *Nat. Rev. Drug Discov.*, 5:295-309, 2006.
Grundy, "Metabolic syndrome: connecting and reconciling cardio-vascular and diabetes worlds," *J. Am. Coll. Cardiol.*, 47:1093-1100, 2006.
Ishizaka et al., "Association between serum albumin, carotid athero-sclerosis, and metabolic syndrome in Japanese individuals," *Atherosclerosis*, 193:373-9, 2007.
Jerkovic et al., "Afamin is a novel human vitamin E-binding glycoprotein characterization and in vitro expression," *J. Proteome. Res.*, 4:889-899, 2005.
Rimm et al., "Reproducibility and validity of an expanded self-administered semiquantitative food frequency questionnaire among male health professionals," *Am. J. Epidemiol.*, 135:1114-1126, 1992.
Voegele et al., "Characterization of the vitamin E-binding properties of human plasma afamin," *Biochemistry*, 41:14532-8, 2002.
Willeit and Kiechl, "Prevalence and risk factors of asymptomatic extracranial carotid artery atherosclerosis. A population-based study," *Arterioscler Thromb.*, 13:661-8, 1993.

* cited by examiner

*Primary Examiner* — Jacob Cheu
(74) *Attorney, Agent, or Firm* — Fulbright & Jaworski LLP

(57) ABSTRACT

The present invention discloses a method for diagnosing the metabolic syndrome by determination of the afamin content in a sample of a body fluid or a tissue sample, wherein the metabolic syndrome is diagnosed if the afamin content in the sample is increased compared to the afamin content in a sample from a person not having the metabolic syndrome.

16 Claims, 3 Drawing Sheets

Unpaired t-test: P = 0.073

METHOD FOR DIAGNOSING THE METABOLIC SYNDROME (MS)

This application is a national phase application under 35 U.S.C. §371 of International Application No. PCT/AT2008/000315 filed 4 Sep. 2008, which claims priority to Austrian Application No. A 1379/2007 filed 4 Sep. 2007. The entire text of each of the above-referenced disclosures is specifically incorporated herein by reference without disclaimer.

The present invention relates to a method for diagnosing the metabolic syndrome.

The metabolic syndrome is characterized by a group of metabolic risk factors including abdominal obesity, atherogenic dyslipidemia (increased plasma levels of total and LDL-cholesterol, triglycerides and free fatty acids), elevated blood pressure, insulin resistance or glucose intolerance resulting in elevated plasma glucose, and prothrombotic and proinflammatory states (5). Patients suffering from the metabolic syndrome are at increased risk of coronary heart disease and other atherosclerotic conditions (such as stroke and peripheral vascular disease) and type 2 diabetes. It is estimated that over 50 million US Americans (with increasing prevalence) suffer from the metabolic syndrome.

The pathogenesis of the metabolic syndrome is multifactorial and polygenic; a long list of lifestyle and genetic parameters has been attributed to ultimately lead to the metabolic disorders described above. These include a sedentary lifestyle, lack of physical exercise, excess intake of dietary fat and its composition as well as several genes affecting glucose and lipoprotein metabolism. Several heritability studies indicated a major role for genetic susceptibility to the metabolic syndrome although the associations were quite weak and the replication of findings has been poor. In addition, recent data indicate a modulating effect of gene-nutrient interactions on the risk of onset for the metabolic syndrome and therapeutic dietary interventions.

On the other hand, due to its multi-risk nature, not only the risk for developing the metabolic syndrome is difficult to estimate, but also its diagnosis and its progression has severe difficulties, because of the high number of parameters that affect the metabolic syndrome patient. The syndrome begins with obesity and/or insulin resistance. In the early stages, the metabolic risk factors (such as elevated apoB, elevated triglycerides, high small LDL, low HDL, elevated glucose, elevated plasminogen activator inhibitor 1, elevated fibrinogen, elevated factor VII, elevated inflammatory cytokines, vascular dysfunction and vascular inflammation, etc.) are often marginally increased, but with time, particularly when obesity increases and other exacerbating factors become involved, the risk factors increase considerably. Therefore, there is a strong need in the field for a reliable diagnosis marker for the metabolic syndrome which correlates well with the disease and which allows an easy diagnosis also for a large number of patients or potential patients to be screened.

The multifactorial nature of the metabolic syndrome has led to a complex drug therapy resulting in polypharmacy (6). There is thus growing interest in therapeutic strategies that might target multiple risk factors more effectively. Diagnosis markers often have also a crucial role in the generation and progression of the disease itself. Therefore, any new and reliable marker correlating well with the disease is also a target for therapeutic intervention to combat the metabolic syndrome.

It is an object of the present invention to provide a method for diagnosing the metabolic syndrome. According to a preferred object, this method should allow a superior diagnosing method with is easily applicable and adaptable to automated testing also for high numbers of samples.

Therefore, the present invention concerns a method for diagnosing the metabolic syndrome by determination of the afamin content in a sample of a body fluid or a tissue sample, wherein the metabolic syndrome is diagnosed if the afamin content in the sample is increased compared to the afamin content in a sample from a person not having the metabolic syndrome. According to the present invention a significant and surprising correlation between the molecular marker afamin and the metabolic syndrome enabled a easy and reliable diagnosis system for metabolic syndrome. Transgenic mice overexpressing the human afamin gene showed significantly elevated serum concentrations of several parameters indicative for the metabolic syndrome when compared to wild type control mice. Afamin was also verified as significant marker in large clinical studies thereby also clearly demonstrating the high predictive value of elevated afamin concentrations for the manifestation of the metabolic syndrome in a large group of patients. With the present invention, the association of elevated afamin concentrations with most known parameters of the metabolic syndrome is provided which has implications for both predictive diagnosis and therapy of the metabolic syndrome.

Afamin is a 87 kDa protein belonging to the albumin group and having many things in common, structurally and in terms of bio-chemistry, with the proteins of this group, such as, e.g., with human serum albumin (HSA), human [alpha]-fetoprotein (AFP) or human vitamin D binding protein. Afamin has already been cloned and sequenced and thus is also available in recombinant form (WO 95/27059). Afamin is a glycoprotein primarily of hepatic origin that is secreted into the circulation. It has been shown that afamin occurs abundantly in plasma and other body fluids like follicular fluid, cerebrospinal and seminal fluid. Apart from its sequence homologies to albumin, little is known about the function of afamin. The possibility has been discussed that afamin has sterol binding sites, yet probably does not bind actin. Due to the existing, yet not overwhelming similarity between afamin and albumin, it is doubted that these proteins bind the same ligands. It has also been shown in vitro and in vivo to possess vitamin E-binding properties (2). The use of afamin for determining the fertility of mammals has been described in WO 01/01148 A1. Afamin has also been identified as a remarkably significant tumour marker for tumours of the reproductive organs (WO2006/079136 A).

Afamin was discovered in 1994 as the fourth member of the human albumin gene family which—as mentioned before—includes albumin, AFP-fetoprotein and vitamin D-binding protein. All four genes map to the chromosomal region 4q11-q22. Afamin is a human plasma glycoprotein with a 15% carbohydrate content and 55% amino acid sequence similarity to albumin. Afamin is also known as alpha-albumin as described in the rat or as alpha-1T-glycoprotein.

In the rat, the expression of afamin starts at birth, and continues to be produced in adult animals. The mean plasma concentration of human afamin was reported between 30 µg/ml and 74 µg/ml. Measurements in vascular and, for the first time, in extravascular body fluids revealed high abundance especially in plasma and follicular fluid (Table 1).

TABLE 1

Concentration of afamin in plasma and extravascular body fluids (1, 2)

| Body fluid | Afamin (µg/ml) (mean ± SD) |
|---|---|
| Plasma | 61.5 ± 13.2 |
| Cerebrospinal fluid | 0.187 ± 0.125 |
| Seminal fluid | 0.566 ± 0.305 |
| Follicular fluid | 37.6 ± 14.4 |

Significant correlations between afamin in plasma and follicular as well as cerebrospinal fluid were found (1). Afamin possesses tocopherol (vitamin E)-binding properties. These in vitro findings of afamin were confirmed by recombinant afamin expressed in transiently transfected COS-1-cells and by ex vivo demonstration of an association between afamin and vitamin E (1). A maximum of 80% displacement of tocopherol was achieved by incubating 2 µM afamin, 60 µM alpha-[$^{14}$C]tocopherol with 100-fold excess of non-labeled alpha- or gamma-tocopherol suggesting that afamin is not only specific for alpha- but also for gamma-tocopherol. Therefore afamin was designated as a vitamin E-binding protein.

Furthermore, two binding sites with different affinity of afamin for vitamin E ($KD_1$=6.3 µM, $KD_2$=22 µM) were described. When both sites are activated, maximal binding (Bmax) of 18 molecules of Vitamin E can be achieved (2). The putative afamin structure with hydrophobic pockets and organization of domains and loops resembles that of albumin. A pattern of disulfide bridges forming a series of nine double loops that define three structural domains was proposed. In line with this model, a Hill coefficient of 1.8 was calculated indicating that afamin could bind pairs of tocopherol. Entry of one molecule of tocopherol would then trigger the binding of another molecule of tocopherol with higher affinity (2).

Afamin circulates in plasma mostly in lipoprotein-free form; a minor fraction of 13% is lipoprotein-associated and elutes in size-exclusion chromatography in small, very dense HDL fractions (1). Since vitamin E is transported in plasma almost exclusively via lipoproteins, ligands and hence a function of afamin in plasma are virtually unknown.

According to the present invention, the elevated level of afamin in patients which are suspected to have or to develop metabolic syndrome confirm this diagnosis with a high reliability. This means that elevated afamin concentrations do not only diagnose an existing metabolic syndrome, but are also predictive for the development of metabolic syndrome at a later stage in life. Accordingly, such prediction is also included in the "diagnosis" according to the present invention. In fact, significance of afamin as a molecular marker for the metabolic syndrome has been confirmed in clinical studies. The elevated afamin content is present if it is apparent in view of the patient's individual "healthy" afamin level or in comparison with a normal level within the population. Accordingly, the physician is the skilled man in the art who finally decides whether the afamin level of a given patient is elevated (and therefore indicative of metabolic syndrome) or not. Depending on the sample nature and detection method, however, also numerical results can be used to define a borderline for series testing. For example, according to a preferred embodiment of the present invention the afamin content in the sample is regarded as increased, if it is at least 10% higher, preferably at least 30% higher, especially at least 50% higher, than the afamin content in a sample from a person not having the metabolic syndrome.

In another preferred embodiment, the afamin content in the sample is regarded as increased, if it is at least 20% higher, preferably at least 40% higher, especially at least 60% higher, than the afamin content in a sample from a person not having the metabolic syndrome.

According to the present invention the afamin content of the sample is determined with a suitable afamin determination method and—due to a comparison with an afamin reference—analysed whether the afamin in the sample is decreased or not. This can be done e.g. by comparing the afamin content in the sample with an afamin standard, such an afamin reference value from a healthy individual or from an individual not having the metabolic syndrome. Alternatively (or in addition), a reference value from a patient having the metabolic syndrome is provided. The reference value may be provided e.g. in form of one or more reference samples, reference tables, reference curves or analogous means as well as combinations thereof. In analysing whether the amount in the sample is increased compared to a "normal" or "healthy" level (with respect to the metabolic syndrome), the skilled man in the art has a number of possibilities. For example, a direct comparison with published reference values of afamin in the body fluid or tissue. In any way, the method according to the present invention does not provide a final medical diagnosis, it provides an afamin value for one sample of unknown metabolic syndrome status or from a person being at risk of or being suspected of having the metabolic syndrome compared to an afamin value of a given or virtual sample verified for having or not having the metabolic syndrome. The final medical diagnosis is then given—independently from the in vitro diagnosing or analysation method according to the present invention—by the individual medically educated person entitled to such a diagnosis.

Often, a person with a normal afamin level ("healthy") is regarded as having an afamin level is serum of 50 to 70 mg. Therefore, according to a preferred embodiment, the person not having the metabolic syndrome is a healthy person with an afamin content of 50 to 70 mg, especially 60 mg, afamin per liter blood serum.

Within the course of the present invention, also other afamin threshold levels above which the afamin level has to be regarded as increased (and still shows a high reliability as marker for the metabolic syndrome) have been determined and correlated to metabolic syndrome. For example, in the study reported in the example section, a sensitivity of 80% and of 60% are present for a specificity cut-off value of 60 mg/l serum. Therefore, in preferred embodiments for serum testing of afamin, a serum sample is regarded as having an increased afamin content if the afamin content is above 62, preferably above 65, more preferred above 67.6, especially above 70 mg, afamin per liter blood serum.

The quantitative levels of afamin also depend on the sample source. Of course, the afamin levels of various body fluids and tissue samples correlate with each other allowing the diagnosis of the present method in a variety of samples of different origin (although, of course, the amount or concentration of afamin differs due to the nature of the sample origin). It is preferred according to the present invention to select the samples according to the needs of a fast and reliable diagnosis. Therefore, preferred body fluids or tissue samples are selected from blood, serum, plasma, cerebrospinal fluid, sperm fluid, follicular fluid, ovarium, testicle or epididymis. Specifically for these sample origins, the correlation of afamin contents has been confirmed.

Although all methods for determining afamin are suitable for the present invention, which allow distinguishing between a normal and a decreased afamin value, the afamin content is preferably determined with anti-afamin antibodies, especially monoclonal antibodies (at least a monoclonal antibody). Such antibodies may comprise a detection marker, preferably a chromogenic, fluorogenic or radioactive marker.

According to a further aspect, the present invention relates to the use of a kit for determining the amount of afamin in a sample of a body fluid or in a tissue sample comprising afamin detection means and an afamin reference for diagnosing the metabolic syndrome. Kits for determination of afamin are well known in the art (e.g. WO 01/01148 or WO 95/27059). Preferably, the use according to the present invention is reduced to practice by applying a method according to the present invention as described above.

Among the usual components of such afamin determination kits, the afamin standard is specifically preferred (e.g. as a standard well in a microtiter ELISA or as standard dot or area on a gene chip or protein (antibody) microarray chip.

According to another aspect, the present invention relates to the use of an afamin-reducing compound for the manufacture of a medicament for the treatment of the metabolic syndrome.

In the course of the present invention, afamin did not only appear as a reliable diagnostic marker but turned out also as an important and significant target for the treatment of the metabolic syndrome. It is therefore possible to treat the metabolic syndrome by reducing the elevated levels of afamin in a patient having the metabolic syndrome. Agents which are able to reduce the afamin content in a patient upon administration ("afamin-reducing compounds") are known to the skilled man in the art. Specifically preferred afamin-reducing compounds to be used for the treatment of metabolic syndrome are selected from the group consisting of afamin antibodies, afamin binding substances, afamin receptors, afamin si-RNA, afamins antisense nucleic acids (DNA, RNA) and mixtures thereof. Specifically the si-RNA technology and afamin antibodies are suitable afamin-reduction means. It is clear that "afamin antibodies" are understood in the broad sense covering all polyclonal or monoclonal antibody preparations, fragments of antibodies, synthetic antibodies (including synthetically rejoined antibodies and fragments), etc. (all, of course, comprising the afamin binding region as essential component).

The present invention is further illustrated by means of the following examples and the figures, yet without being restricted thereto.

Figure 4:
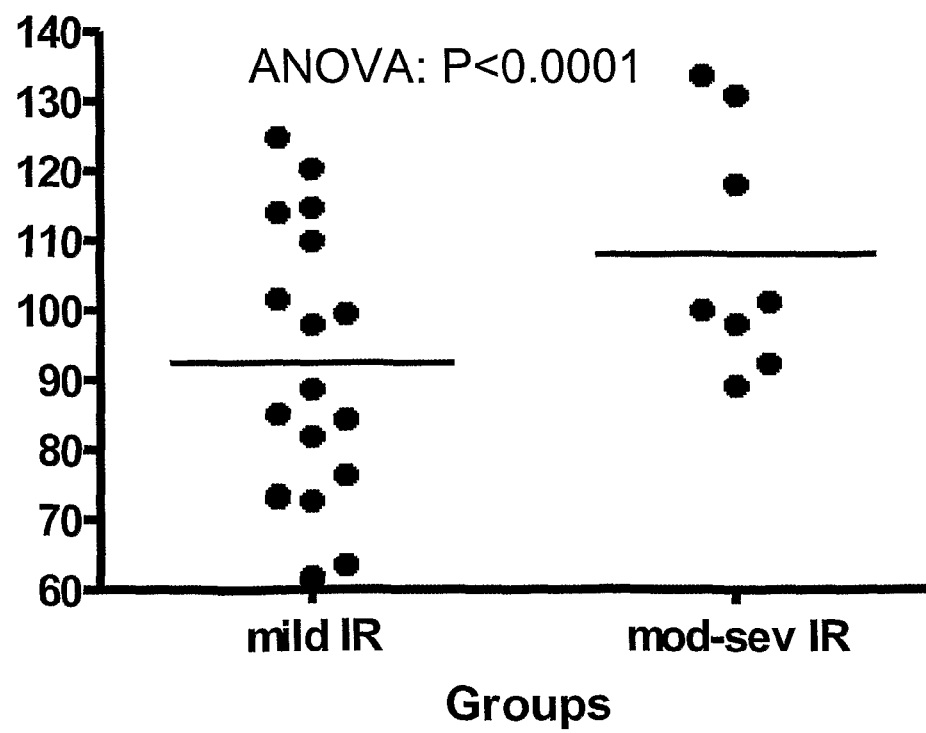

FIG. 4. shows Afamin plasma concentrations (y axis in microgram/ml) in subgroups PCOS patients with mild (n=17) and moderate to severe insulin resistance (IR, n=8).

EXAMPLES

1. Materials and Methods

Afamin Transgenic Animals.

FVB/N mice overexpressing human afamin were created using a construct of human afamin cDNA and a liver-specific promoter. The construct was microinjected into male pronuclei of fertilised eggs which were then transferred into uteri of pseudopregnant mice. The putative founders were genotyped and animals positive for the transgene were bred with wild-type mice. Resulting off-spring were studied concerning transgene transmission, number of transgene integrations and copy number. Homozygous animals were generated; 6 transgenic lines with copy numbers between 3 and 180 were obtained. Plasma levels of human afamin in these mice reached up to 30 mg/l which is equivalent to approximately 50% of human afamin plasma levels and approximately 6 times higher compared with the endogenous mouse afamin levels. No grossly obvious phenotype differing from wild-type mice of the same genetic FVB/N background was noticed so far in young transgenic animals.

Human Population Studies.

In order to confirm possible findings observed in the transgenic mouse model also in human populations, afamin was measured in the large population-based Bruneck study (3) and correlated with any possibly available parameter/phenotype. An association between afamin plasma concentrations and these phenotypes in human populations would not only confirm the preliminary mouse data but would also indicate causality between afamin and the respective clinical phenotype and would therefore provide a novel predicitive tool in the early diagnosis of these phenotypes/diseases. Since longitudinal follow-up over 15 years is available in the Bruneck Study, a possible causal role of afamin could be further supported.

The Bruneck Study is a highly recognized, well phenotyped study which has been meticulously planned and performed as a population-based prospective observation study with an extremely high responder rate of the invited study population.

The study design and survey area has been described in detail previously (3). At the study entry (year 1990) the study population comprised an age- and sex-stratified random sample of all inhabitants of Bruneck (Bolzano Province, Italy) aged 40 to 79 years (125 women and 125 men in each of the fifth to the eighth decades). There was a participation of 93.6% among individuals invited and complete data assessment in 919 subjects. Further examinations very similar to the baseline examination were performed in 1995, 2000 and 2005 enabling a follow-up period of 15 years. All participants gave informed consent before enrolment in the study.

History, Clinical Evaluation and End Points.

Demographic data, medications (including hormonal therapy) and clinical history as well as atherosclerosis risk profile including smoking and drinking behaviour were recorded by questionnaire as well as standardized interview. Diet was assessed by using an interviewer-administered semiquantitative food frequency questionnaire (96 items) similar to versions of the instruments that have been validated in other epidemiologic studies (4). Leisure and working time physical activity was evaluated by a questionnaire.

All participants underwent a complete clinical examination with cardiological and neurological priority described recently in detail (3). Cardiovascular disease endpoints during follow-up were fatal and non-fatal myocardial infarction and ischemic stroke and transient ischemic attack. Self-reported data were verified from hospital records, death certificates, as well as information from general practitioners and supplemented by a thorough screening of the regional hospital database for diseases of interest.

Scanning Protocol and Definition of Ultrasound End Points.

The internal (bulbous and distal segments) and common (proximal and distal segments) carotid arteries were scanned by ultrasound on either side (3). Atherosclerotic lesions were identified by two ultrasound criteria: (1) wall surface (protrusion into the lumen or roughness of the arterial boundary) and (2) wall texture (echogenicity). The maximum radial diameter of plaques was assessed in each of the eight vessel segments with the ultrasound beam directed through the center of the vessel. Scanning was performed at baseline as well as at each of the three following examinations by the same experienced sonographer, who was blinded for the subjects' clinical and laboratory characteristics. Based on the follow-up evaluation two epidemiologically and etiologically different stages of atherogenesis were differentiated: (1) Early atherosclerosis was defined by the occurrence of new plaques in previously normal segments. (2) Advanced atherogenesis was assumed whenever the relative increase in the maximum plaque diameter between 2 examinations exceeded the double measurement error of the method and a narrowing of the lumen (stenosis)>40% occurred.

Laboratory Investigations in the Bruneck Study.

At the 1990 baseline investigation and the three follow-up examinations, blood samples were taken from the antecubital vein after subjects had fasted and abstained from smoking for at least 12 hours. After centrifugation, plasma was stored at −70° C. Afamin was measured in samples from the 1995 examination as described (1) by an ELISA using an affinity-purified polyclonal anti-afamin antibody at the concentration of 5 μg/ml for coating and a peroxidase-conjugated mouse monoclonal antibody (N13) for detection. The rabbit polyclonal and mouse monoclonal antibodies were obtained by standard immunological techniques after immunization with purified human afamin that also served as primary standard. The precise protein concentration of the primary standard was determined by amino acid composition analysis.

Other variables which were already measured during the first two examinations or in context with other subprojects of the Bruneck Study include: vitamin E, glucose, HbA1c, insulin, 2-hour-insulin, thyroid hormones (T3, T4, TSH), total, HDL and LDL cholesterol, triglycerides, apolipoprotein A-I and B, lipoprotein(a) and apolipoprotein(a) phenotype, oxidized LDL, beta-caroten, AT-III, D-dimer, PT, PTT, fibrinogen, PAI, Factor V Leiden, potassium, total protein, bilirubin, ferritin, transferrin, ceruloplasmin, C-reactive protein and leptin.

2. Results

Transgenic Animals.

1 year old male and female animals had a significantly higher body weight than age-matched wildtype mice. Most remarkably, plasma concentrations of total cholesterol, triglycerides and glucose were significantly increased whereas HDL-cholesterol was not different compared to sex-matched wild-type littermates (Table 2). These preliminary data correlate to an involvement of afamin in lipid disorders subsequently leading to phenotypes such as obesity, diabetes and metabolic syndrome.

TABLE 2

Body weight and lipid and glucose plasma concentrations in 1-year-old fasted afamin-transgenic and wild-type mice of the same FVB/N genetic background.

| | Body weight (g) | Cholesterol (mg/dl) | HDL-cholesterol (mg/dl) | Triglycerides (mg/dl) | Glucose (mg/dl) |
|---|---|---|---|---|---|
| Afamin-transgenic mice (n = 8) | 38 +/− 4 | 186 +/− 9 | 95 +/− 6 | 157 +/− 15 | 111 +/− 25 |
| Wild-type (FVB/N) controls (n = 8) | 32 +/− 3 | 154 +/− 15 | 102 +/− 21 | 102 +/− 11 | 82 +/− 15 |
| P | <0.01 | <0.05 | n.s. | <0.001 | <0.01 |

Bruneck Study.

The distribution of afamin plasma concentrations and numerous demographic and life-style parameters, vascular risk factors and other laboratory variables in the Bruneck study are shown in Table 3. The evaluation was performed according to tertile groups of Afamin (low, medium and high); the whole study group consisted of 826 individuals.

TABLE 3

Distribution of demographic and life style parameters, vascular risk factors and other laboratory variables according to tertile group for afamin (n = 826)

| | TERTILE GROUP FOR AFAMIN | | | |
|---|---|---|---|---|
| VARIABLES | 1-low | 2-medium | 3-high | P |
| Afamin (mg/l) | | | | |
| Median | 48.1 | 61.5 | 76.2 | |
| Range | 23.1-55.4 | 55.5-67.6 | 67.7-137.7 | |
| Demographic variables | | | | |
| Age (years) | 57.7 ± 11.4 | 58.0 ± 11.2 | 58.2 ± 10.8 | 0.645 |
| Sex (%) | | | | 0.646 |
| Men | 53.1 | 41.8 | 55.4 | |
| Premenopausal women | 12.0 | 11.0 | 3.6 | |
| Postmenopausal women | 34.9 | 47.3 | 41.0 | |
| Social status (%) | | | | 0.118 |
| Low | 62.9 | 59.0 | 61.5 | |
| Medium | 24.4 | 23.4 | 16.9 | |
| High | 12.7 | 17.6 | 21.6 | |
| Life-style variables, diet and body composition | | | | |
| Smoking (cigarettes per day) | 1.9 ± 5.1 | 2.6 ± 6.3 | 3.2 ± 7.2 | 0.017 |
| Alcohol consumption (g/day) | 23.2 ± 30.8 | 21.3 ± 29.7 | 26.2 ± 32.3 | 0.249 |
| Physical activity (sport score) | 2.4 ± 0.9 | 2.3 ± 1.0 | 2.3 ± 0.8 | 0.586 |
| Waist-to-hip ratio (cm/cm) | 0.91 ± 0.07 | 0.92 ± 0.07 | 0.95 ± 0.07 | <0.001 |
| Body-mass index (kg/m$^2$)§ | 23.9 ± 3.4 | 25.5 ± 3.3 | 27.6 ± 3.9 | <0.001 |
| Obesity (BMI >30, %) | 3.6 | 10.6 | 27.3 | <0.001 |
| Lipids and lipoproteins | | | | |
| LDL cholesterol (mg/dL) | 134.6 ± 33.6 | 149.5 ± 37.9 | 151.9 ± 39.0 | <0.001 |
| HDL cholesterol (mg/dL) | 62.3 ± 17.6 | 59.0 ± 15.5 | 54.2 ± 14.3 | <0.001 |
| Triglycerides (mg/dL) | 93.5 ± 39.7 | 135.4 ± 87.9 | 167.8 ± 87.5 | <0.001 |
| Free fatty acids (mmol/L) | 0.664 ± 0.499 | 0.671 ± 0.510 | 0.724 ± 0.489 | 0.030 |
| Lipoprotein(a) (mg/dL) | 25.0 ± 31.2 | 28.0 ± 33.6 | 25.4 ± 32.6 | 0.321 |
| Apolipoprotein AIV (mg/dL) | 14.9 ± 3.7 | 14.1 ± 3.4 | 13.8 ± 3.6 | 0.001 |
| Apolipoprotein AI (mg/dL) | 166.2 ± 29.7 | 168.1 ± 26.9 | 162.0 ± 25.8 | 0.066 |
| Apolipoprotein B100 (mg/dL) | 102.5 ± 25.0 | 117.6 ± 31.3 | 128.1 ± 32.0 | <0.001 |
| Vascular risk factors and other laboratory variables | | | | |
| Systolic blood pressure (mmHg) | 141.8 ± 18.7 | 149.4 ± 20.6 | 153.6 ± 20.9 | <0.001 |
| Diastolic blood pressure (mmHg) | 84.2 ± 8.6 | 87.4 ± 9.0 | 89.6 ± 9.2 | <0.001 |
| Hypertension (%) | 54.9 | 69.6 | 80.2 | <0.001 |
| Fasting glucose (mg/dL) | 96.3 ± 13.0 | 101.3 ± 24.9 | 109.3 ± 30.3 | <0.001 |
| 2-hr glucose (mg/dL) (n = 750) | 97.2 ± 35.4 | 108.6 ± 39.2 | 130.4 ± 69.6 | <0.001 |
| Diabetes (%) | 4.7 | 6.6 | 18.3 | <0.001 |
| Hba1$_c$ (%) | 5.4 ± 0.4 | 5.5 ± 0.7 | 5.7 ± 0.9 | <0.001 |

TABLE 3-continued

Distribution of demographic and life style parameters, vascular risk factors and other laboratory variables according to tertile group for afamin (n = 826)

| VARIABLES | TERTILE GROUP FOR AFAMIN | | | P |
|---|---|---|---|---|
| | 1-low | 2-medium | 3-high | |
| HOMA-IR | 2.7 ± 1.9 | 3.5 ± 2.5 | 5.7 ± 8.3 | <0.001 |
| Ferritin (µg/L) | 103 ± 134 | 124 ± 136 | 174 ± 206 | <0.001 |
| Creatinine (mg/dL) | 0.9 ± 0.2 | 0.9 ± 0.2 | 1.0 ± 0.2 | 0.633 |
| γ-GT (U/L) | 25.6 ± 20.8 | 33.4 ± 31.6 | 50.2 ± 58.4 | <0.001 |
| hs-CRP (mg/L) | 3.5 ± 7.3 | 3.0 ± 5.7 | 3.2 ± 4.2 | 0.004 |
| Fibrinogen (mg/dL) | 288.6 ± 91.1 | 288.8 ± 71.1 | 290.4 ± 63.2 | 0.775 |
| Antithrombin III (%) | 97.9 ± 10.8 | 101.4 ± 10.2 | 98.4 ± 13.2 | 0.654 |
| Vitamin levels | | | | |
| Tocopherol (µmol/L) (n = 407) | 23.4 ± 8.6 | 24.9 ± 10.0 | 26.6 ± 12.3 | 0.013 |
| Retinol (µmol/L) (n = 409) | 2.2 ± 1.0 | 2.5 ± 1.0 | 2.6 ± 1.1 | 0.002 |
| β-carotinoids (µmol/L) (n = 409) | 0.9 ± 0.8 | 0.8 ± 0.7 | 0.5 ± 0.4 | 0.002 |
| Other carotinoids (µmol/L) (n = 409) | 0.2 ± 0.3 | 0.1 ± 0.2 | 0.1 ± 0.1 | 0.001 |
| 25-hydroxy-vitamin D (ng/mL) | 30.4 ± 12.2 | 32.7 ± 12.7 | 32.6 ± 11.9 | 0.043 |

Figure 1:
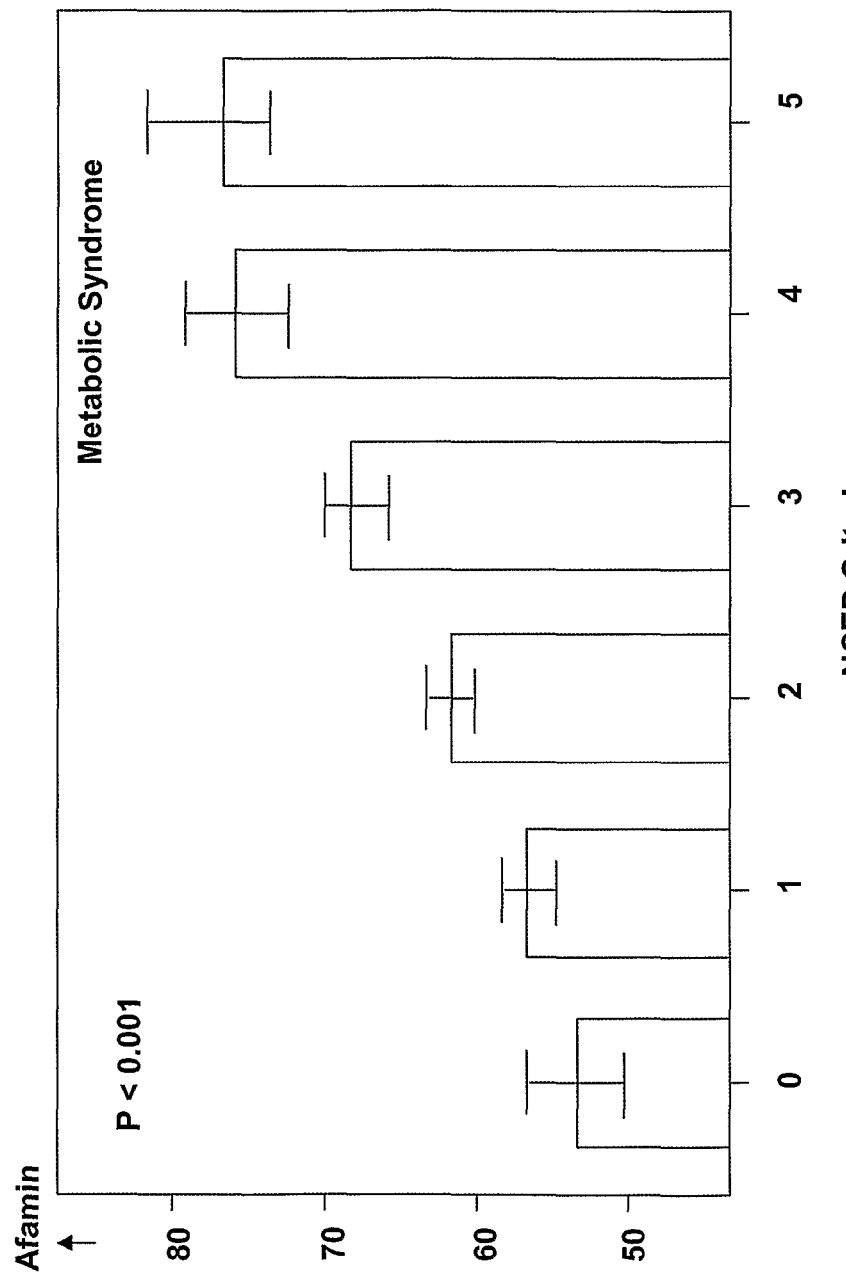
FIG. 1 shows the positive correlation between afamin plasma concentrations and the number of NCEP criteria (a value >2 is considered as diagnosed metabolic syndrome)

In FIG. 1, the positive correlation between afamin plasma concentrations and the number of NCEP criteria is shown. A value >2 is considered as diagnosed metabolic syndrome in this set-up. This correlation clearly demonstrates the high predictive value of elevated afamin concentrations for the manifestation of the metabolic syndrome.

Figure 2:
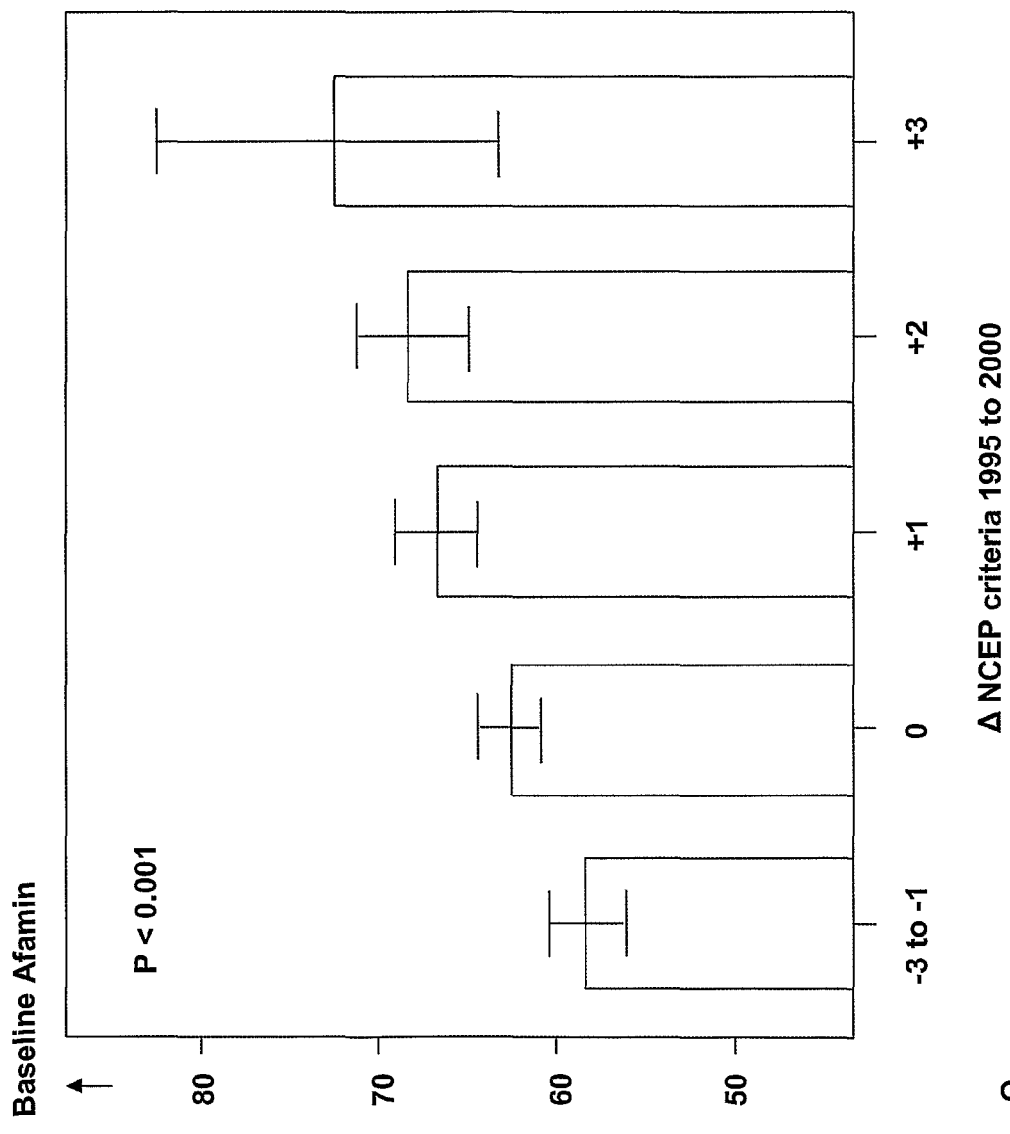
FIG. 2 shows the positive correlation between afamin concentrations and the increase in number of NCEP criteria (Delta NCEP) between the visits in 1995 and 2000.

In FIG. 2 the positive correlation between afamin concentrations and the increase in number of NCEP criterias (Delta NCEP) between the visits in 1995 and 2000 is shown. This is an even stronger argument for the causative role of afamin concentrations for the development of the metabolic syndrome and elegantly confirms the findings of our data from transgenic animals.

The association of afamin with the Metabolic Syndrome and Insulin Resistance (IR) was further investigated and supported by a study of afamin concentrations (measured by ELISA) in the plasma of female patients with the polycystic ovary syndrome (PCOS), a benign gynecological condition frequently associated with the Metabolic Syndrome. PCOS patients were compared with healthy controls and patients with IR but no PCOS.

Figure 3:
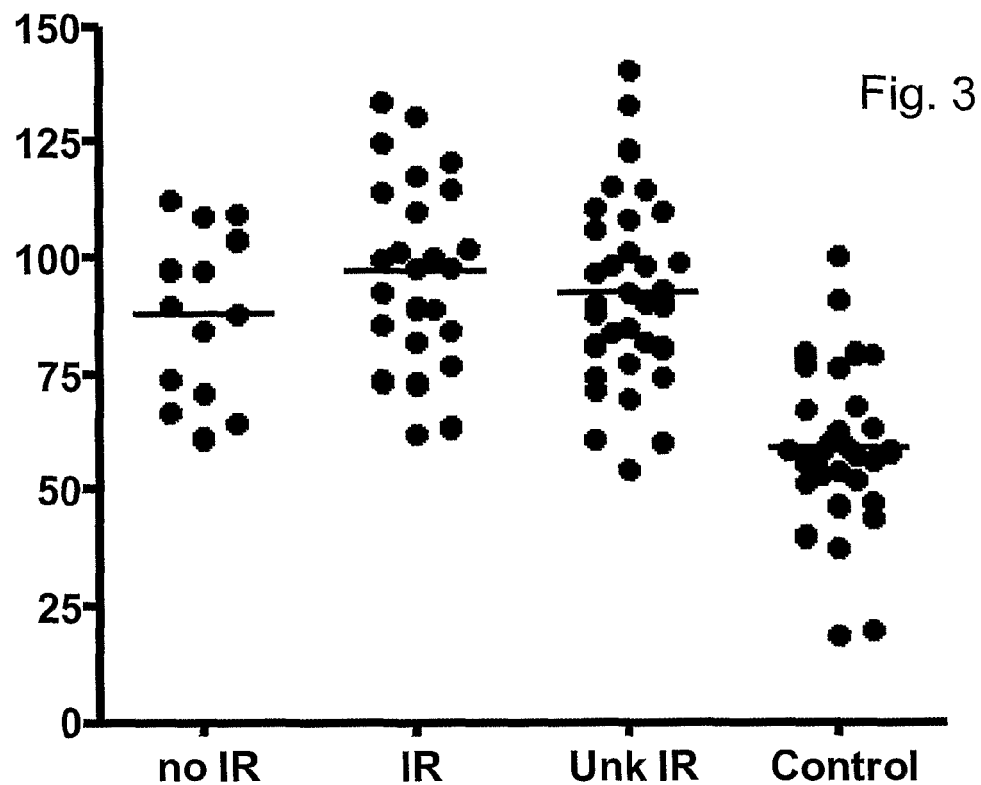
FIG. 3 shows afamin concentrations in patients with PCOS (Polycystic Ovary Syndrome, n=39) compared with normal controls (n=31) and patients with IR (insulin resistance) without PCOS (UnkIR, n=33); y-Axis: afamin concentration in plasma in microgram per ml.

FIG. 3 shows significantly elevated afamin plasma concentrations in PCOS patients regardless of the presence of insulin resistance. A trend of association between afamin and IR was, however, observed in addition, and, as shown in FIG. 4, also between afamin and the severity of IR. This observation was based, however, only preliminarily on a yet small sample size.

These results show not only an association of afamin with key parameters of the metabolic syndrome but, supported by the transgenic mice data, a causal role of afamin for the development of this epidemic disease. The present data therefore confirm a high diagnostic potential for afamin to predict the metabolic syndrome. Accordingly, the present finding of the association of elevated afamin concentrations with most known parameters of the metabolic syndrome has implications for both predictive diagnosis and therapy. The suggested functional role of afamin in lipid/lipoprotein and glucose metabolism shows that this protein is an exiting novel key target for therapeutic intervention to combat the modern epidemic metabolic syndrome.

REFERENCES

1. Jerkovic, L., Voegele, A. F., Chwatal, S., Kronenberg, F., Radcliffe, C. M., Wormald, M. R., Lobentanz, E. M., Ezeh, B., Eller, P., Dejori, N., et al. 2005. Afamin is a novel human vitamin E-binding glycoprotein characterization and in vitro expression. J Proteome Res 4:889-899.
2. Voegele, A. F., Jerkovic, L., Wellenzohn, B., Eller, P., Kronenberg, F., Liedl, K. R., and Dieplinger, H. 2002. Characterization of the vitamin E-binding properties of human plasma afamin. Biochemistry 41:14532-14538.
3. Willeit, J., and Kiechl, S. 1993. Prevalence and risk factors of asymptomatic extracranial carotid artery atherosclerosis. A population-based study. Arterioscler Thromb 13:661-668.
4. Rimm, E. B., Giovannucci, E. L., Stampfer, M. J., Colditz, G. A., Litin, L. B., and Willett, W. C. 1992. Reproducibility and validity of an expanded self-administered semiquantitative food frequency questionnaire among male health professionals. Am J Epidemiol 135:1114-1126; discussion 1127-1136.
5. Grundy, S. M. 2006. Metabolic syndrome: connecting and reconciling cardiovascular and diabetes worlds. J Am Coll Cardiol 47:1093-1100.
6. Grundy, S. M. 2006. Drug therapy of the metabolic syndrome: minimizing the emerging crisis in polypharmacy. Nat Rev Drug Discov 5:295-309.

The invention claimed is:

1. A method of diagnosing a metabolic syndrome comprising determining afamin content in a sample of a body fluid or a tissue sample, wherein a metabolic syndrome is diagnosed if the afamin content in the sample is significantly elevated compared to that of a person not having the metabolic syndrome.

2. The method of claim 1, wherein the afamin content in the sample is regarded as significantly elevated if it is at least 10% higher than that of a person not having the metabolic syndrome.

3. The method of claim 2, wherein the afamin content in the sample is regarded as significantly elevated if it is at least 20% higher than that of a person not having the metabolic syndrome.

4. The method of claim 3, wherein the afamin content in the sample is regarded as significantly elevated if it is at least 40% higher than that of a person not having the metabolic syndrome.

5. The method of claim 4, wherein the afamin content in the sample is regarded as significantly elevated if it is at least 60% higher than that of a person not having the metabolic syndrome.

6. The method of claim 1, wherein a person not having the metabolic syndrome is defined as a healthy person with an afamin content of 50 to 70 mg afamin per liter blood serum.

7. The method of claim 1, wherein a person not having the metabolic syndrome is defined as a healthy person with an afamin content of about 60 mg afamin per liter blood serum.

8. The method of claim 1, wherein a serum sample has a significantly elevated afamin content if the afamin content is above 62 mg afamin per liter blood serum.

9. The method of claim 8, wherein a serum sample has a significantly elevated afamin content if the afamin content is above 65 mg afamin per liter blood serum.

10. The method of claim 9, wherein a serum sample has a significantly elevated afamin content if the afamin content is above 67.6 mg afamin per liter blood serum.

11. The method of claim 10, wherein a serum sample has a significantly elevated afamin content if the afamin content is above 70 mg afamin per liter blood serum.

12. The method of claim 1, wherein the body fluid or tissue sample is blood, serum, plasma, cerebrospinal fluid, sperm fluid, follicular fluid, ovarian, testicle, or epididymis.

13. The method of claim 1, wherein the afamin content is determined with an anti-afamin antibody.

14. The method of claim 13, wherein the antibody is a monoclonal antibody.

15. The method of claim 13, wherein said antibody comprises a detection marker.

16. The method of claim 15, wherein the detection marker is a chromogenic, fluorogenic, or radioactive marker.

* * * * *

UNITED STATES PATENT AND TRADEMARK OFFICE
CERTIFICATE OF CORRECTION

PATENT NO.         : 8,137,922 B2
APPLICATION NO.    : 12/676528
DATED              : March 20, 2012
INVENTOR(S)        : Hans Dieplinger et al.

Page 1 of 1

It is certified that error appears in the above-identified patent and that said Letters Patent is hereby corrected as shown below:

In column 1, line 7, delete "A 1379/2007" and insert --A 1378/2007-- therefor.

Signed and Sealed this
First Day of May, 2012

David J. Kappos
*Director of the United States Patent and Trademark Office*